United States Patent
Sarsani et al.

(10) Patent No.: US 10,941,088 B1
(45) Date of Patent: Mar. 9, 2021

(54) METHOD AND REACTOR FOR OXIDATIVE COUPLING OF METHANE

(71) Applicant: SABIC Global Technologies B.V., Bergen op Zoom (NL)

(72) Inventors: Sagar Sarsani, Pearland, TX (US); David West, Bellaire, TX (US); Vemuri Balakotaiah, Bellaire, TX (US); Tian Gu, Richmond, TX (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 16/965,370

(22) PCT Filed: May 2, 2019

(86) PCT No.: PCT/US2019/030329
§ 371 (c)(1),
(2) Date: Jul. 28, 2020

(87) PCT Pub. No.: WO2019/213352
PCT Pub. Date: Nov. 7, 2019

Related U.S. Application Data

(60) Provisional application No. 62/665,663, filed on May 2, 2018.

(51) Int. Cl.
*C07C 2/84* (2006.01)
*B01J 35/02* (2006.01)
*B01J 8/08* (2006.01)

(52) U.S. Cl.
CPC .............. *C07C 2/84* (2013.01); *B01J 8/082* (2013.01); *B01J 8/085* (2013.01); *B01J 35/023* (2013.01);
(Continued)

(58) Field of Classification Search
None
See application file for complete search history.

(56) References Cited

U.S. PATENT DOCUMENTS 4,876,409 A 10/1989 Leyshon et al.
6,087,545 A 7/2000 Choudhary et al.
(Continued)

FOREIGN PATENT DOCUMENTS

AU 2013355038 B2 6/2014
CA 3061564 A1 11/2018
(Continued)

OTHER PUBLICATIONS

International Search Report and Written Opinion of the International Search Authority (ISA/US) dated Jul. 5, 2019 in counterpart International PCT Patent Application No. PCT/US2019/030329.
(Continued)

*Primary Examiner* — Colin W. Slifka
(74) *Attorney, Agent, or Firm* — Grady K. Bergen; Paul I. Herman; Griggs Bergen LLP

(57) ABSTRACT

A method of autothermal oxidative coupling of methane (OCM) utilizes introducing a methane-containing feedstock and an oxygen-gas-containing feedstock into a reactor (10) as a flowing mixture (18) with a space time of 500 ms or less. The reactor (10) contains a catalyst bed (20) of an OCM catalyst that contacts the flowing mixture and wherein the catalyst bed (20) has a heat Peclet number ($Pe_h$) of from 5 or less, a mass Peclet number ($Pe_m$) of from 5 or more, and a transverse Peclet number (P) of from 1 or less while contacting the flowing mixture. The methane and oxygen of the feedstocks are allowed to react within the reactor (10) to form methane oxidative coupling reaction products. A reactor (10) for carrying out the OCM reaction is also disclosed.

19 Claims, 2 Drawing Sheets

(52) U.S. Cl.
CPC ............... *B01J 2208/00938* (2013.01); *B01J 2208/00982* (2013.01); *C07C 2521/08* (2013.01); *C07C 2521/10* (2013.01); *C07C 2523/04* (2013.01); *C07C 2523/14* (2013.01); *C07C 2523/652* (2013.01); *C07C 2523/656* (2013.01)

(56) References Cited

U.S. PATENT DOCUMENTS

| | | |
|---|---|---|
| 6,096,934 A | 8/2000 | Rekoske |
| 8,815,080 B2 | 8/2014 | Sundaram |
| 9,352,295 B2 | 5/2016 | Rafique et al. |
| 2004/0235969 A1 | 11/2004 | Espinoza et al. |
| 2012/0129064 A1 | 5/2012 | Simakov et al. |
| 2015/0152025 A1 | 6/2015 | Cizeron et al. |
| 2015/0321974 A1 | 11/2015 | Schammel et al. |
| 2015/0329439 A1 | 11/2015 | Nyce et al. |
| 2017/0240488 A1 | 8/2017 | West et al. |

FOREIGN PATENT DOCUMENTS

| | | |
|---|---|---|
| WO | WO2004103936 A1 | 12/2004 |
| WO | WO2007126811 A2 | 11/2007 |
| WO | WO2015057753 A1 | 4/2015 |

OTHER PUBLICATIONS

Sarsani, et al., Autothermal oxidative coupling of methane with ambient feed temperature, Chemical Engineering Journal, 2017, pp. 486-496, vol. 328.

Mleczko et al.,Catalytic oxidative coupling of methane—reaction engineering aspects and process schemes, Fuel Processing Technology, 1995, pp. 217-248, vol. 42.

Wang et al.,Oxidative coupling of methane over oxide-supported sodium-manganese catalysts, Journal of Catalysis, 1995, pp. 390-402, vol. 155.

Lunsford, Catalytic conversion of methane to more useful chemicals and fuels: a challenge for the 21st century. Catalysis Today, 2000, pp. 165-174, vol. 63.

Wozny et al., Oxidative Coupling of Methane: A Design of Integrated Catalytic processes, Chemical Engineering Transactions, 2010, pp. 1399-1404, vol. 21.

Leyshon, Thin bed reactor for conversion of Methane to higher Hydrocarbons, A. Holmen et al., Natural Gas Conversion, Studies in Surface Science and Catalysis, 1991, pp. 497-507, vol. 61.

Dautzenberg et al.,Catalyst and reactor requirements for the oxidative coupling of methane, Catalysis Today, 1992, pp. 503-509, vol. 13.

Kalakkunnath, Oxidative Coupling of Methane to Ethylene by Siluria Process, IHS Chemical Process Economics Program, PEP review, Apr. 2004, pp. i-41, Jul. 2004.

Wang et al., Catalytic oxidation of methane to methanol initiated in a gas mixture of hydrogen and oxygen, J. Chem. Soc., Chem. Commun., 1994, pp. 2209-2210.

Canadian Official Action dated Nov. 20, 2020 in counterpart Canadian Patent Application No. 3,096,475.

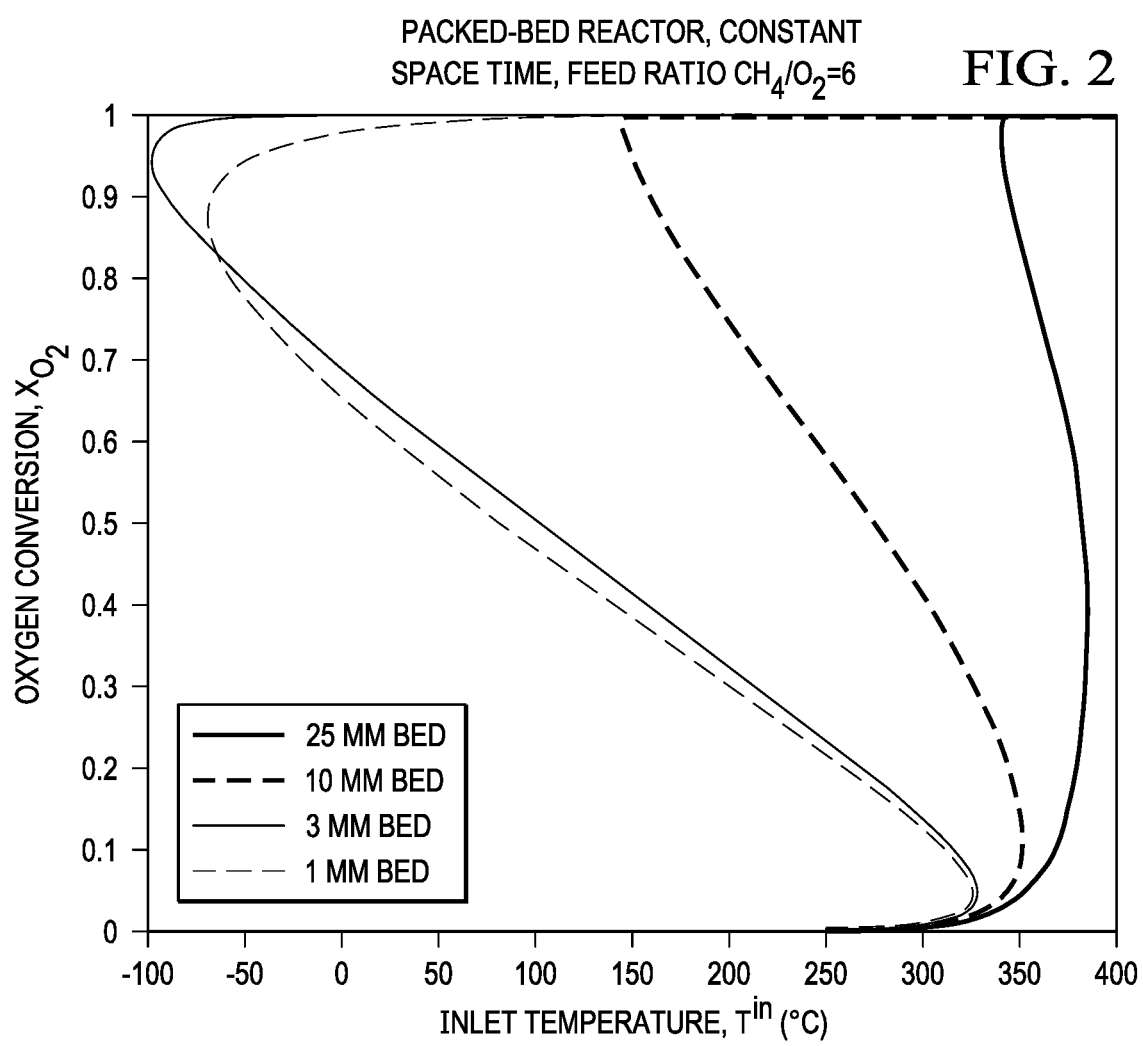

METHOD AND REACTOR FOR OXIDATIVE COUPLING OF METHANE

CROSS-REFERENCE TO RELATED APPLICATIONS

This application is a national stage application under 35 U.S.C. § 371 of International PCT Application No. PCT/US2019/030329, filed May 2, 2019, which claims the benefit of U.S. Provisional Application No. 62/665,663, filed May 2, 2018, each of which is incorporated herein by reference in its entirety.

TECHNICAL FIELD

The invention relates to the conversion of methane and oxygen to $C_2$ and higher hydrocarbons and reactor designs for such conversion.

BACKGROUND

Methane can be used to produce ethane and/or ethylene through the oxidative coupling of methane (OCM) reaction. While extensive research and development has been devoted to this reaction, the reaction largely remains inefficient on a commercial scale. One of the key challenges is the high reaction temperature (typically greater than 750° C.) required to make the reaction proceed. The need for such a high temperature is due to the bond strength (bond dissociation energy) of the tetrahedral C—H bonds in methane, which is 104 kcal per mol (kcal/mol). This C—H bond strength makes methane less reactive and difficult to undergo oxidative conversion to form ethylene.

The oxidative coupling of methane reaction can be represented by Equations (1) and (2) below:

$$2CH_4 + O_2 \rightarrow C_2H_4 + 2H_2O \quad \Delta H = -67.4 \text{ kcal/mol} \quad (1)$$

$$2CH_4 + \tfrac{1}{2}O_2 \rightarrow C_2H_6 + H_2O \quad \Delta H = -84.6 \text{ kcal/mol} \quad (2)$$

As shown in Equations (1) and (2), oxidative conversion of methane to ethylene or ethane is exothermic. Excess heat produced from these reactions can push conversion of methane to carbon monoxide and carbon dioxide rather than the desired $C_2$ hydrocarbon product, as shown in Equations (3) and (4) below:

$$CH_4 + 1\tfrac{1}{2}O_2 \rightarrow CO + 2H_2O \quad \Delta H = -82.8 \text{ kcal/mol} \quad (3)$$

$$CH_4 + 2O_2 \rightarrow CO_2 + 2H_2O \quad \Delta H = -95.9 \text{ kcal/mol} \quad (4)$$

It should be noted that the heats of reaction for Equations (1) to (4) are given per mole of oxygen consumed. The excess heat from the reaction in Equations (3) and (4) further exacerbates this situation, thereby substantially reducing the selectivity of ethylene production when compared with carbon monoxide and carbon dioxide production.

Equations (5) through (8), set forth below, illustrate the chemical pathway in which the OCM reaction can occur in the presence of a catalyst:

$$O_2 + 2[*] \rightarrow 2[O] \quad (5)$$

$$CH_4 + [O] \rightarrow CH_3 + [OH] \quad (6)$$

$$2CH_3 \rightarrow C_2H_6 \rightarrow C_2H_4 \rightarrow CO_X \quad (7)$$

$$2[OH] \rightarrow [O] + [*] + H_2O \quad (8)$$

where * is a vacant catalytic surface site. The coupling of methyl radicals in Equation (7) occurs in the gas phase while the formation of $C_2H_4$ and $CO_X$ may either be catalytic or in the gas phase. The remaining reactions Equations (5), (6), and (8) occur on the catalyst.

There are two practical problems that have prevented the development of commercially feasible OCM processes. One is the very large heat of reaction (Equations 1-4); and two is the very high temperature to initiate the reaction (typically 700-950° C.). There is no commercially available liquid heat transfer fluid capable of operating at such high temperatures. Consequently, the only way to cool a reactor at this range of temperature is with very inefficient gas phase coolants (e.g., air, steam, ethane, etc.). In a cooled multi-tubular fixed bed reactor, the methane conversion must be limited by the oxygen concentration in the feed to less than about 8% in order to avoid a runaway reaction. A runaway reaction is one in which the temperature rise within the catalyst bed is high enough to damage or deactivate the catalyst or to increase the production of by-products ($CO_x$).

The present invention overcomes these disadvantages, with the methods and reactors described herein being particularly useful for commercial scale OCM operations.

SUMMARY

A method of carrying out autothermal oxidative coupling of methane (OCM) is carried out by introducing a methane-containing feedstock and an oxygen-gas-containing feedstock into a reactor as a flowing mixture with a space time of 500 ms or less. The reactor contains a catalyst bed of an OCM catalyst that contacts the flowing mixture and wherein the catalyst bed has a heat Peclet number ($Pe_h$) of from 5 or less, a mass Peclet number ($Pe_m$) of from 5 or more, and a transverse Peclet number (P) of from 1 or less while contacting the flowing mixture. The methane and oxygen of the feedstocks are allowed to react within the reactor to form methane oxidative coupling reaction products.

In specific embodiments, the catalyst bed may have different configurations. In one, the catalyst bed is configured as at least one of a layer of OCM catalyst formed as catalyst particles having a particle size of from 0.1 mm to 3 mm. In another the catalyst bed is at least one monolithic body of one of a ceramic or metal material having pores or channels with a pore or channel size from 0.1 to 5 mm, the monolithic body having an OCM catalyst material present on at least all or a portion of the surface of the monolithic body. In another configuration, the catalyst bed is at least one monolithic body of one of a ceramic or metal material having pores or channels with a pore or channel size from 0.1 to 5 mm, and wherein the pores or channels contain an OCM catalyst powder.

The methane-containing feedstock may be introduced into the reactor at a temperature of from −100° C. to 300° C. In certain instances, the methane-containing feedstock is introduced into the reactor at a temperature of from −20° C. to 150° C.

The reactor may be operated at a space time of from 500 ms or less, and in some instances from 100 ms or less. The catalyst bed temperature may range from 500° C. to 1000° C. In some cases, the catalyst bed temperature may range from 800° C. to 950° C.

The OCM catalyst may be comprised of at least one of $La_2CeO_2$, $SrO/La_2O_3$, $CeO_2$, $La_2O_3$—$CeO_2$, $Ca/CeO_2$, $Mn/Na_2WO_4$, $Li_2O$, $Na_2O$, $Cs_2O$, $WO_3$, $Mn_3O_4$, CaO, MgO, SrO, BaO, CaO—MgO, CaO—BaO, Li/MgO, MnO, $W_2O_3$, $SnO_2$, $Yb_2O_3$, $Sm_2O_3$, $SrO/La_2O_3$, $La_2O_3$, $Ce_2O_3$, La/MgO, and combinations thereof.

In certain embodiments, the heat Peclet number ($Pe_h$) is from 1 or less, the mass Peclet number ($Pe_m$) is from 10 or more, and the transverse Peclet number (P) is from 0.1 or less.

An oxidative coupling reactor is also provided. The oxidative coupling reactor comprises a reactor that defines a reaction chamber and has at least one inlet for introducing a flowing methane-containing feedstock and an oxygen-gas-containing feedstock into the reaction chamber. A catalyst bed is positioned within the reaction chamber that receives the flowing methane-containing feedstock and an oxygen-gas-containing feedstock as a flowing mixture with a space time of 500 ms or less. The catalyst bed contains an OCM catalyst, the catalyst bed configured to have a heat Peclet number ($Pe_h$) of from 5 or less, a mass Peclet number ($Pe_m$) of from 5 or more, and a transverse Peclet number (P) of from 1 or less as gases pass through the catalyst bed. A reactor outlet is in fluid communication with the reaction chamber for removing reaction products from the reactor.

In specific embodiments, the catalyst bed comprises a layer of OCM catalyst formed as catalyst particles having a particle size of from 0.1 mm to 3 mm. In some cases, the layer of OCM catalyst is from 5 to 20 particles deep.

The catalyst bed may comprise at least one monolithic body of one of a ceramic and metal material having pores or channels with a pore or channel size from 0.1 to 5 mm, the monolithic body having an OCM catalyst material present on at least all or a portion of the surface of the monolithic body, in some embodiments. In certain cases, the at least one monolithic body may have a thickness of from 5 mm to 50 mm In other embodiments, the catalyst bed may comprise at least one monolithic body of one of a ceramic and metal material having pores or channels with a pore or channel size from 0.1 to 5 mm, and wherein the pores or channels contain an OCM catalyst powder. In some cases, the monolithic body may have a thickness of from 5 mm to 100 mm at least one monolithic body has a thickness of from 5 mm to 100 mm. The catalyst powder may have a particle size of less than 400 microns.

The catalyst used for the reactor may be an OCM catalyst selected from at least one of $La_2CeO_2$, $SrO/La_2O_3$, $CeO_2$, $La_2O_3$—$CeO_2$, $Ca/CeO_2$, $Mn/Na_2WO_4$, $Li_2O$, $Na_2O$, $Cs_2O$, $WO_3$, $Mn_3O_4$, $CaO$, $MgO$, $SrO$, $BaO$, $CaO$—$MgO$, $CaO$—$BaO$, $Li/MgO$, $MnO$, $W_2O_3$, $SnO_2$, $Yb_2O_3$, $Sm_2O_3$, $SrO/La_2O_3$, $La_2O_3$, $Ce_2O_3$, $La/MgO$, and combinations thereof.

BRIEF DESCRIPTION OF THE DRAWINGS

For a more complete understanding of the embodiments described herein, and the advantages thereof, reference is now made to the following descriptions taken in conjunction with the accompanying figures, in which:

FIG. 2 is a plot of simulated OCM reactions from Example 2 that were carried out for a packed bed reactor configured in accordance with particular embodiments described herein and showing the effect of catalyst bed depth and feed temperatures on oxygen conversion and the Peclet numbers for the different catalyst bed depths.

DETAILED DESCRIPTION

Figure 1:
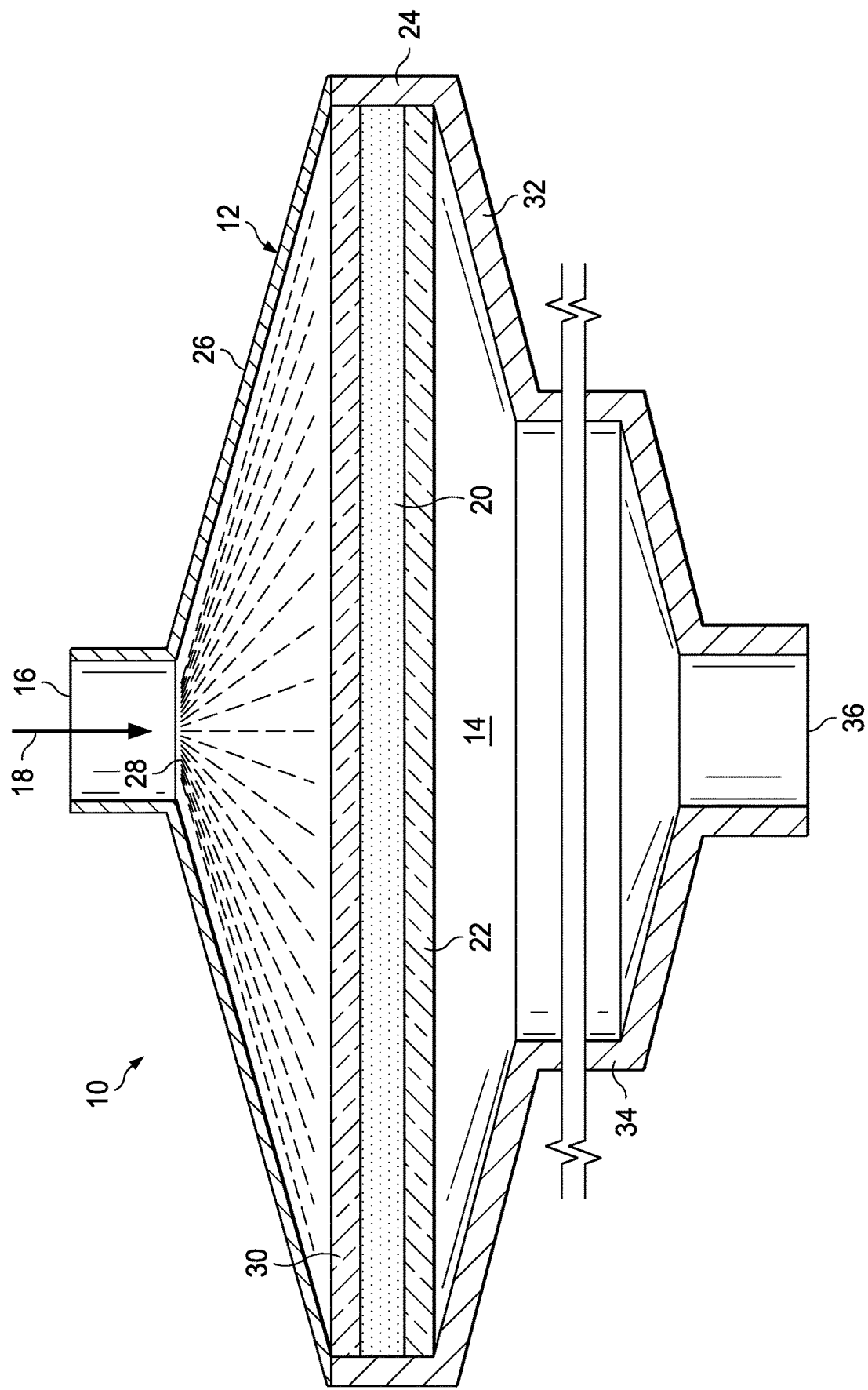
FIG. 1 is a schematic of an exemplary OCM reactor configured in accordance with particular embodiments described herein.

Oxidative coupling of methane has a very large heat of reaction resulting in large adiabatic temperature rises (typically >500° C.). In addition, the reaction has very high temperature sensitivity (i.e., an increase in reaction rate with increasing temperature) because of the high energy barrier for activating methane. These two characteristics make it difficult, if not impossible, to remove the heat of reaction as fast as it is released, making the reaction uncontrollable.

It has been discovered that by the use of a unique catalyst bed and very high space velocities, so that the reaction takes place under near adiabatic conditions, very high yields and higher volumetric productivity from OCM can be obtained per unit volume of catalyst. This also allows the use of low cost adiabatic reactors, as contrasted with the use of cooled multi-tubular reactors or the use of complex fluidized bed reactors.

By the use of the particular configuration of catalyst bed and operating state, adiabatic or near-adiabatic auto-thermal oxidative coupling of methane can be achieved. While adiabatic conditions are desired, in practice only near-adiabatic conditions can be maintained. This is true even though reference is commonly made to the use of adiabatic reactors. Those skilled in the art will recognize that there is some heat transfer in such adiabatic reactors so they are not perfectly adiabatic. Accordingly, the use of the term "adiabatic" throughout this disclosure may therefore refer to such near-adiabatic conditions, which can be defined as from 10% or 5% or less heat transfer or heat loss from the reactor (relative to the total heat generated). Furthermore, as used herein, the expression "auto-thermal" with respect to the OCM reaction described means that only the heat produced by the reaction itself is used to carry out the reaction. This means that once the reaction commences, no heating from other sources is provided to carry out the oxidative coupling reaction when it reaches steady state.

It should be noted in the description, if a numerical value, concentration or range is presented, each numerical value should be read once as modified by the term "about" (unless already expressly so modified), and then read again as not so modified unless otherwise indicated in context. Also, in the description, it should be understood that an amount range listed or described as being useful, suitable, or the like, is intended that any and every value within the range, including the end points, is to be considered as having been stated. For example, "a range of from 1 to 10" is to be read as indicating each and every possible number along the continuum between about 1 and about 10. Thus, even if specific points within the range, or even no point within the range, are explicitly identified or referred to, it is to be understood that the inventor appreciates and understands that any and all points within the range are to be considered to have been specified, and that inventor possesses the entire range and all points within the range.

The unique catalyst bed design and its operation provide several advantages. First, it expands the region of the auto-thermal operating conditions. This includes broadening the range of oxygen concentration that can be used, the feed temperature range, and feed flowrates over which the auto-thermal operation is possible. Second, it leads to the existence of an ignited state within the catalyst bed with ambient feed and the optimum catalyst temperature, which promotes catalyst stability. Third, it leads to higher yields of the OCM reaction products by making the temperature almost constant (and within the optimum temperature range) over the entire catalyst bed. Fourth, it minimizes dispersion of reactants and thus maximizes the concentration driving force for the reaction, thus maximizing the rate of reaction. The catalyst bed is designed so that the mass flow rate of reactants by convection is about ten times higher than the rate of dispersion of reactants. The ratio of convection to dispersion is controlled or determined by the mass Peclet number. These characteristics make it possible to obtain higher yields of OCM reaction products (e.g., $C_2$ hydrocarbons) and higher volumetric productivity than can be obtained with conventional adiabatic reactors, as well as cooled tubular and fluidized bed reactors.

Referring to FIG. 1, a schematic representation of an exemplary reactor 10 employing the novel catalyst bed and in which the OCM reaction may be carried out is shown. The reactor 10 includes a reactor vessel 12 that defines an interior reaction chamber 14. One or more inlets 16 for introducing a flowing feed mixture 18 of a methane-containing feedstock and an oxygen-gas-containing feedstock into the interior of the reactor vessel 12. The reactor 10 is configured as an adiabatic reactor (or near-adiabatic) to prevent or reduce heat transfer or loss through the walls of the reactor vessel 12. Typically, the reactor 10 will be oriented for vertical flow, with the inlet 16 being located on the top or bottom of the reactor vessel 12. In the embodiment shown, the inlet 16 is located at the top of the reactor vessel 12 so that fluid flow is directed downward through the reactor 10.

A catalyst bed 20 is positioned within the reaction chamber 14 of the reactor vessel 12. The catalyst bed 20 may be supported on a catalyst bed support 22, such as a perforated ceramic support plate. As will be described in more detail later on, the catalyst bed is configured to meet certain requirements related to the dimensionless Peclet (Pe) numbers. The catalyst bed 20 may be configured to have a rather large width or diameter but a relatively shallow depth or thickness. As used herein with reference to the catalyst bed 20 and its components, the terms "length," "thickness," "depth," and the like, as it refers to the catalyst bed refers to the linear distance as measured axially between the opposite upstream and downstream surfaces of the catalyst bed 20. The flow through the reactor 10 may be axial and parallel to a central longitudinal vertical axis (not shown) that passes through the center of the reactor vessel 12 and through the catalyst bed 20. In certain embodiments, the catalyst bed thickness may range from 5 mm to 200 mm.

The width or diameter of the catalyst bed 20 may be significantly greater than the catalyst bed depth or thickness so that the catalyst bed 20 has a generally flat or pancake-shaped configuration. In certain embodiments, the catalyst bed 20 may have a width or diameter of several meters (e.g., from 1 to 5 meters).

In some embodiments, the reactor vessel 12 may have a generally cylindrical configuration along generally its entire length, with the length of the reactor vessel 12 greatly exceeding its width or diameter. In the embodiment shown, however, the wall portion 24 of the reactor vessel 12 that immediately surrounds and houses the catalyst bed 20 may be generally cylindrical in shape with other portions of the reactor vessel being conical or frusto-conical. As is shown in FIG. 1, the reactor vessel 12 may have conical-shaped or sloped reactor walls that extend from the cylindrical wall portion 24 surrounding the catalyst bed 20. In the embodiment shown, a conical or frusto-conical upstream reactor wall 26 joins the upstream end of the cylindrical wall 24 and tapers radially inwardly along its longitudinal axis to the inlet 16. A gas flow distributor 28 may be provided in the upstream section of the reactor vessel 12 defined by the upstream reactor wall 26 to facilitate distributing the flowing gas mixture from the inlet 16 across the width of the upstream surface of the catalyst bed 20. In certain embodiments, the need for a flow distributor may be eliminated by use of a conical diffuser with walls tapered at angle of from 3 to 10 degrees.

As shown in FIG. 1, a radiation shield 30, such as a ceramic foam, may be provided above the catalyst bed in certain embodiments.

A conical or frusto-conical downstream reactor wall 32 may join the downstream end of the cylindrical wall 24 and taper radially inward along its longitudinal axis to an intermediate downstream section of the reactor vessel 12. The intermediate section 34 may be formed from a generally cylindrical portion of the reactor vessel 12 that has a width or diameter that is less than that of the cylindrical wall 24 surrounding the catalyst bed 20.

An outlet 36 of the reactor vessel 12 receives the products from the reaction chamber 14 where they are discharged from the reactor vessel 12 and may be collected and stored or directed to other processing equipment for further processing. This may include cracking and/or quenching of the reaction products, which may be carried out in other vessels or equipment external to the reactor 10 or reactor vessel 12 for such purposes.

The catalyst used for the catalyst bed 20 may not be limited to any particular type of catalyst provided it is suitable for the OCM reaction and facilitates meeting the necessary requirements for the catalyst bed configuration and operation, as is described in more detail later on. The OCM catalyst should have a high enough activity to provide the desired OCM conversion with the high space velocities or space time used and reaction conditions, as described herein. One or more different OCM catalysts can be used. These may be supported catalysts, bulk metal catalysts, and/or unsupported catalysts, or combinations of these. The support can be active or inactive. The catalyst support can include MgO, $Al_2O_3$, $SiO_2$, or the like. All the support materials are those currently available or that can be formed from those processes known in the art. These may include precipitation/co-precipitation, sol-gel, templates/surface derivatized metal oxides synthesis, solid-state synthesis, of mixed metal oxides, microemulsion techniques, solvothermal, sonochemical, combustion synthesis, etc. One or more of the catalyst can include one or more metals or metal compounds thereof. Non-limiting catalytic metals include Li, Na, Ca, Cs, Mg, La, Ce, W, Mn, Ru, Rh, Ni, and Pt, and combinations and alloys of these. Non-limiting examples of suitable catalysts include: (1) La on a MgO support; (2) Na, Mn, and $La_2O_3$ on an aluminum support; (3) Na and Mn on a silicon dioxide support; (4) $Na_2WO_4$ and Mn on a silicon dioxide support, and combinations of these. Non-limiting examples of some particular catalysts that can be used include $La_2CeO_2$, $SrO/La_2O_3$, $CeO_2$, $La_2O_3$—$CeO_2$, $Ca/CeO_2$, $Mn/Na_2WO_4$, $Li_2O$, $Na_2O$, $Cs_2O$, $WO_3$, $Mn_3O_4$, CaO, MgO, SrO, BaO, CaO—MgO, CaO—BaO, Li/MgO, MnO, $W_2O_3$, $SnO_2$, $Yb_2O_3$, $Sm_2O_3$, $SrO/La_2O_3$, $La_2O_3$, $Ce_2O_3$, La/MgO, and combinations thereof.

The catalyst of the catalyst bed 20 may take several different forms. In one form, this may include a shallow layer of catalyst particles having particle sizes of from 0.1 mm to 10 mm, more particularly from 0.1 mm, 0.2 mm, 0.3 mm, 0.4 mm, 0.5 mm, 0.6 mm, 0.7 mm, 0.8 mm, 0.9 mm, or 1 mm to 2 mm, 3 mm, 4 mm, 5 mm, 6 mm, 7 mm, 8 mm, 9 mm, or 10 mm. In certain embodiments the catalyst particles making up the shallow layer may have particle size ranging from 0.1 mm to 3 mm, 4 mm, or 5 mm. The catalyst particles making up the catalyst bed may be of the same or different sizes. The layer of catalyst particles forming the catalyst bed may be from 5 mm to 200 mm deep, and in certain embodiments from 5 mm to 25 mm deep. The catalyst particles may rest on the catalyst bed support 22. Such support 22 may include, but is not limited to a perforated ceramic support plate, quartz fiber mats, stainless steel screens, stainless steel coated with fused silica, etc. The catalyst particles can be of eggshell type or constitute a coating on a high conductivity non-catalytic particle. The catalyst bed can be a mix of OCM catalyst and non-catalytic high conductivity particles.

In another form, the catalyst bed 20 may be composed of one or more porous monolithic bodies. The monolithic body may be a ceramic or metal material having pores or channels with a pore or channel size (i.e., the transverse width or diameter) of from 0.1 mm to 5 mm, more particularly from 0.5 mm to 2.0 mm. The length or thickness of the monolithic bodies forming the catalyst bed 20 may range from 5 mm to 200 mm, more particularly from 5 mm, 10 mm, 20 mm, 30 mm, or 40 mm to 50 mm, 60 mm, 70 mm, 80 mm, 90 mm, or 100 mm or more. All or a portion of the pore channels of the monolithic body may be oriented parallel to the central axis or direction of flow through the reactor 10. In other embodiments, the pores may be non-parallel to the direction of flow or may be randomly oriented, such as a ceramic or metal foam material. The pores should be continuous or contiguous through the thickness of the monolithic body to allow passage of gases therethrough from the upstream side to the downstream side of the catalyst bed 20. The cross-sectional shape of the pores may vary but in particular embodiments may be circular, oval, square, rectangular, polygonal, etc. In other embodiments, all or a portion of the cross-sectional shape of the pores may be irregular or non-uniform in shape.

The monolithic body or bodies are either formed from or are provided with an OCM catalyst material present on at least all or a portion of the surfaces of the monolithic body. In particular, at least all or a portion of the surfaces of the pore channels are coated with such OCM catalyst material, such as those OCM catalyst material described previously. The amount of OCM catalyst material provided on the monolithic bodies is that sufficient to carry out the OCM reaction, as described herein.

In still another form, the catalyst bed 20 may be composed of one or more porous monolithic bodies similar to those described above. The pore sizes may be the same as those previously described, i.e., pore or channel size (i.e., the transverse width or diameter) of from 0.1 mm to 5 mm, more particularly from 0.5 mm to 2.0 mm. The length or thickness of the monolithic bodies forming the catalyst bed may range from 5 mm to 200 mm, more particularly from 5 mm, 10 mm, 20 mm, 30 mm, or 40 mm to 50 mm, 60 mm, 70 mm, 80 mm, 90 mm, or 100 mm or more. Unlike the monolithic bodies previously described, the surfaces of the monolithic may not be coated or provided with an OCM catalytic material, although in certain instances they may be coated with such an OCM catalytic material, as well. Instead, all or a portion of the pore channels of the monolithic body or bodies are filled with OCM catalyst particles or powder, such as the OCM catalyst particle materials described previously. The OCM catalyst particles or powder may have a particle size of from 400 microns, 300 microns, 200 microns, 100 microns or less. All or a portion of the pores of the monolithic are filled with the OCM catalyst particles or powder to carry out the OCM reaction.

The reactor/catalyst bed is configured to give selected dimensionless Peclet numbers based upon the flow through the reactor 10. The feed gas mixture is delivered to the reactor to provide a flowing gas mixture with a high enough velocity to provide a space time that is from 500 milliseconds (ms) or less. In particular embodiments, the flowing mixture flow provides a space time of from 500 ms, 400 ms, 300 ms, 200 ms, 100 ms, 50 ms, 25 ms, or 10 ms or less.

Based upon such flow rates to provide the selected space time during the autothermal reaction, the dimensionless Peclet (Pe) numbers provide a means for configuring the catalyst bed containing the OCM catalyst, as previously described. The Pe numbers provide a means for determining the optimal catalyst bed depth. This can be achieved by calculating the three dimensionless Peclet numbers, i.e., the Heat Peclet Number ($Pe_h$), the Mass Peclet Number ($Pe_m$), and the Transverse Peclet Number (P).

The Heat Peclet Number ($Pe_h$) is defined in Equation (9) below:

$$Pe_h = \frac{uLC_{pv}}{k_{b,eff}} \qquad (9)$$

where, u is the superficial gas velocity, L is the catalyst bed depth or thickness, $C_{pv}$ is the volumetric specific heat of the reaction mixture, and $k_{b,eff}$ is the effective bed thermal conductivity. $Pe_h$ is the ratio of thermal conduction time in the axial direction to the convection time within the catalyst bed. In configuring the OCM catalyst bed of the reactor, a catalyst bed for the selected catalyst bed length or thickness and selected operating conditions, such as a space time of 500 ms or less, when subjected to the flowing gas mixture provides a $Pe_h$ of from 5 or less. In certain embodiments, the catalyst bed under the selected operating conditions when subjected to the flowing gas mixture provides a $Pe_h$ of from 5, 4, 3, 2, or 1 or less, more particularly from 2 or 1 or less.

The Mass Peclet Number ($Pe_m$) is defined in Equation (10) below:

$$Pe_m = \frac{uL}{D_{m,eff}} \qquad (10)$$

where, $D_{m,eff}$ is the effective axial mass dispersion coefficient. $Pe_m$ is the ratio of mass dispersion time in the axial direction to the convection time. In configuring the OCM catalyst bed of the reactor, a catalyst bed for the selected catalyst bed length or thickness and selected operating conditions when subjected to the flowing mixture provides a $Pe_m$ of from 5 or more. In certain embodiments, the catalyst bed under the selected operating conditions provides a $Pe_m$ of from 5, 6, 7, 8, 9, or 10 or more, more particularly from 8, 9, or 10 or more.

The Transverse Peclet Number (P) is defined in Equation (11) below:

$$P = \frac{u}{k_c a_v L} \qquad (11)$$

where, $k_c$, is the local mass transfer coefficient and $a_v$ is the specific surface area of the catalyst (external catalyst surface area per unit volume of bed). P is the ratio of external mass transfer time (from the flow to the catalyst surface) to the convection time. In configuring the OCM catalyst bed of the reactor, a catalyst bed for the selected catalyst bed length or thickness and selected operating conditions when subjected to the flowing mixture provides a P of from 1 or less.

In certain embodiments, the catalyst bed under the selected operating conditions provides a P of from 1, 0.9, 0.8, 0.7, 0.6, 0.5, 0.4, 0.3, 0.2, or 0.1 or less, more particularly from 0.3, 0.2, or 0.1 or less. Reactors with OCM catalyst beds that are operated in the autothermal state at high gas flow rates to provide a low space time of from 500 ms or less and that meet the specified Peclet number parameters presented above can be used in an adiabatic autothermal operation in which the feed gas mixture can be used as the coolant and which provides increased yields of OCM reaction products of $C_2+$ hydrocarbons and high volumetric productivity than with conventional OCM reactors.

The gaseous feedstocks used with the reactor and method include hydrocarbons and oxygen. The hydrocarbon feedstock may be methane, natural gas, light-alkane gases (e.g., $C_2$-$C_6$), etc. All or a majority portion of the hydrocarbon feedstock may comprise methane in certain embodiments. The methane-containing gas may be a pure methane gas or may be methane gas source containing other gases. In certain instance, the feed stream may be predominantly methane (i.e., >50 mol %) or entirely methane. In particular embodiments, the feed stream may be composed of natural gas, which may have a methane content of from 85 mol % to 97 mol % or more, or other hydrocarbon-rich gases. In some cases the hydrocarbon feedstock may be a pretreated feed that has been treated to remove undesirable components, such as sulfur-containing compounds and the like. The oxygen-containing gas may be air, oxygen-enriched air, or pure oxygen gas. In particular embodiments, the oxygen-containing gas is pure oxygen. The reactant gas mixture may contain other gases, provided such gases do not negatively affect the reaction. These can include nitrogen ($N_2$), carbon dioxide ($CO_2$), hydrogen ($H_2$), etc.

The OCM reaction is ignited in a manner that avoids transient states at which the temperatures would destroy or damage the OCM catalyst of the catalyst bed. In particular embodiments, the reaction startup methods described in Applicant's U.S. Patent Application No. 62/457,119, filed Feb. 7, 2017, which is incorporated herein by reference in its entirety for all purposes, may be used. As is described U.S. Patent Application No. 62/457,119, during the reaction startup, the feed gas mixture having a selected HC/$O_2$ or $CH_4$/$O_2$ molar ratio, which may range from 3:1 to 40:1, is initially heated to a temperature of at least 400° C., more particularly from 400° C. to 750° C. The heated feed gas mixture is introduced into the OCM reactor so that the catalyst bed is also heated and the OCM reaction commences. The feed gas mixture may be introduced to provide a space time of from 0.1 ms to 1000 ms. Upon ignition, the temperature and/or HC/$O_2$ or $CH_4$/$O_2$ molar ratio can be incrementally reduced over a startup period. Additionally, the flow rate may be adjusted to provide a shorter space time. Once a selected operating temperature is achieved, the OCM reaction remains ignited and the reactor can be maintained in an autothermal state.

Once the OCM reaction is in an ignited state, the reaction is made to operate continuously in an autothermal state by supplying feed gas for the oxidative coupling reaction to the reactor at a rate and at a low enough temperature to compensate for the heat of reaction generated in the reactor. In this way, the feed gas serves as a coolant as the reactor is heated to a higher temperature by the heat generated by the oxidative coupling reaction in the reactor. Once the reactor reaches the autothermal state, the feed gas mixture to the reactor may comprise a hydrocarbon gas (HC) or methane-containing gas, which may contain at least some portion of methane ($CH_4$), and oxygen gas ($O_2$). The HC/$O_2$ or $CH_4$/$O_2$ molar ratio of the feed gas mixture may range from 2.5:1 to 10:1, more particularly from 3:1 to 9:1.

The temperature of the feed gas mixture during the autothermal state, which is a HC-containing or methane-containing feedstock along with an oxygen-gas-containing feedstock, is introduced into the reactor at a temperature of from −100° C. to 300° C. In particular embodiments the temperature of the mixed gas feedstock introduced into the reactor ranges from −20° C. to 150° C., more particularly from −20° C., −10° C., or 0° C. to 50° C., 100° C., or 150° C. The cooler feedstock gas mixture introduced into the reactor and the high space velocity facilitates maintaining the catalyst bed temperature at the desired temperature during the autothermal state even while the OCM generates a significant amount of heat during the reaction.

The OCM reactor is operated in the ignited or autothermal state to provide a catalyst bed temperature of from 500° C. to 1000° C. In particular embodiments, the reactor is operated to provide a catalyst bed temperature of from 800° C. to 950° C. in the ignited or autothermal state. The reactor may be operated at a pressure of from 0.1 MPa to 1 MPa, more particularly from 0.1 MPa to 0.5 MPa in the autothermal state.

The products produced from the OCM reaction include ethane, ethylene, as well as other $C_2+$ hydrocarbon products along with carbon oxides like CO and $CO_2$.

The following examples serve to further illustrate various embodiments and applications.

EXAMPLES

Example 1

A 41 mm I.D. alumina reactor was used as the near adiabatic reactor for each run. Different height catalyst beds of the reactor containing OCM catalyst particles were used in the reactions. The reactions were started using those startup procedures described in U.S. Patent Application No. 62/457,119. At steady state, a gaseous feed mixture that included the reactant gases $CH_4$ and $O_2$ at selected $CH_4$:$O_2$ molar ratios were introduced into the reactor. Analysis of a sample stream at the center of the catalyst bed showed that both the conversion and C2+ selectivity were higher with the shorter bed when a similar space time was maintained. The results are presented in Table 1 below:

TABLE 1

| Bed height, mm | 25 | | 10 | | |
|---|---|---|---|---|---|
| $O_2$ conversion, % | 97.8 | 98.0 | 99.6 | 99.2 | 99.5 |
| Flow rate, L/min | 28.5 | 28.1 | 10.0 | 10.0 | 11.6 |
| Feed $CH_4$/$O_2$ ratio | 6.6 | 5.5 | 6.6 | 5.6 | 5.9 |
| Selectivities, % | | | | | |
| $C_2+$ | 56.1 | 53.0 | 67.6 | 63.8 | 65.2 |
| CO | 10.3 | 11.3 | 5.3 | 5.6 | 5.7 |
| $CO_2$ | 33.7 | 35.7 | 27.1 | 30.5 | 29.1 |

Estimated Peclet numbers for the two reactor bed configurations are summarized in Table 2 below:

TABLE 2

| Bed ID × Height | 41 mm × 25 mm | 41 mm × 10 mm |
|---|---|---|
| $Pe_h$ | 21 | 3.2 |
| $Pe_m$ | 94 | 29 |

Example 2

FIG. 2 shows the oxygen ($O_2$) conversion obtained during computer simulated OCM reactions for a packed bed reactor containing an OCM catalyst at different catalyst bed depths. The reactions were those with a mixed gas feed at a $CH_4/O_2$ molar ratio of 6 at different feed temperatures using a feed velocity to provide a constant space time. The Peclet numbers for each catalyst bed depth are provided in Table 3 below:

TABLE 3

| Bed Depth | $Pe_m$ | $Pe_h$ | P | $T^{in}$ at extinction (° C.) | Max $T_s$ at extinction (° C.) |
|---|---|---|---|---|---|
| 25 mm | 94 | 25 | 0.007 | 341 | 1016 |
| 10 mm | 34 | 4.7 | 0.009 | 145 | 873 |
| 3 mm | 5.5 | 0.45 | 0.011 | −100 | 680 |
| 1 mm | 0.75 | 0.05 | 0.014 | −69 | 662 |

While the invention has been shown in some of its forms, it should be apparent to those skilled in the art that it is not so limited, but is susceptible to various changes and modifications without departing from the scope of the invention based on experimental data or other optimizations considering the overall economics of the process. Accordingly, it is appropriate that the appended claims be construed broadly and in a manner consistent with the scope of the invention.

We claim:

1. A method of carrying out autothermal oxidative coupling of methane (OCM) comprising:
   introducing a methane-containing feedstock and an oxygen-gas-containing feedstock into a reactor as a flowing mixture with a space time of 500 ms or less, the reactor containing a catalyst bed of an OCM catalyst that contacts the flowing mixture and wherein the catalyst bed has a heat Peclet number ($Pe_h$) of from 5 or less, a mass Peclet number ($Pe_m$) of from 5 or more, and a transverse Peclet number (P) of from 1 or less while contacting the flowing mixture; and
   allowing the methane and oxygen of the feedstocks to react within the reactor to form methane oxidative coupling reaction products.

2. The method of claim 1, wherein:
   the catalyst bed comprises at least one of the following:
   a layer of OCM catalyst formed as catalyst particles having a particle size of from 0.1 mm to 3 mm;
   at least one monolithic body of one of a ceramic or metal material having pores or channels with a pore or channel size from 0.1 to 5 mm, the monolithic body having an OCM catalyst material present on at least all or a portion of the surface of the monolithic body;
   at least one monolithic body of one of a ceramic or metal material having pores or channels with a pore or channel size from 0.1 to 5 mm, and wherein the pores or channels contain an OCM catalyst powder.

3. The method of claim 1, wherein:
   the catalyst bed comprises at least one monolithic body of one of a ceramic or metal material having pores or channels with a pore or channel size from 0.1 to 5 mm, and wherein the pores or channels contain an OCM catalyst powder having a particle size of less than 400 microns.

4. The method of claim 1, wherein:
   the methane-containing feedstock is introduced into the reactor at a temperature of from −100° C. to 300° C.

5. The method of claim 1, wherein:
   the methane-containing feedstock is introduced into the reactor at a temperature of from −20° C. to 150° C.

6. The method of claim 1, wherein:
   the reactor is operated at a space time of from 100 ms or less.

7. The method of claim 1, wherein:
   the catalyst bed temperature is from 500° C. to 1000° C.

8. The method of claim 1, wherein:
   the catalyst bed temperature is from 800° C. to 950° C.

9. The method of claim 1, wherein:
   the OCM catalyst is comprised of at least one of $La_2CeO_2$, $SrO/La_2O_3$, $CeO_2$, $La_2O_3$—$CeO_2$, $Ca/CeO_2$, $Mn/Na_2WO_4$, $Li_2O$, $Na_2O$, $Cs_2O$, $WO_3$, $Mn_3O_4$, CaO, MgO, SrO, BaO, CaO—MgO, CaO—BaO, Li/MgO, MnO, $W_2O_3$, $SnO_2$, $Yb_2O_3$, $Sm_2O_3$, $SrO/La_2O_3$, $La_2O_3$, $Ce_2O_3$, La/MgO, and combinations thereof.

10. The method of claim 1, wherein:
    the heat Peclet number ($Pe_h$) is from 1 or less, the mass Peclet number ($Pe_m$) is from 10 or more, and the transverse Peclet number (P) is from 0.1 or less.

11. An oxidative coupling reactor comprising:
    a reactor that defines a reaction chamber and having at least one inlet for introducing a flowing methane-containing feedstock and an oxygen-gas-containing feedstock into the reaction chamber;
    a catalyst bed positioned within the reaction chamber that receives the flowing methane-containing feedstock and an oxygen-gas-containing feedstock as a flowing mixture with a space time of 500 ms or less, the catalyst bed containing an OCM catalyst, the catalyst bed configured to have a heat Peclet number ($Pe_h$) of from 5 or less, a mass Peclet number ($Pe_m$) of from 5 or more, and a transverse Peclet number (P) of from 1 or less as gases pass through the catalyst bed; and
    a reactor outlet in fluid communication with the reaction chamber for removing reaction products from the reactor.

12. The reactor of claim 11, wherein:
    the catalyst bed comprises a layer of OCM catalyst formed as catalyst particles having a particle size of from 0.1 mm to 3 mm.

13. The reactor of claim 12, wherein:
    the layer of OCM catalyst is from 5 to 20 particles deep.

14. The reactor of claim 11, wherein:
    the catalyst bed comprises at least one monolithic body of one of a ceramic and metal material having pores or channels with a pore or channel size from 0.1 to 5 mm, the monolithic body having an OCM catalyst material present on at least all or a portion of the surface of the monolithic body.

15. The reactor of claim 14, wherein:
    the at least one monolithic body has a thickness of from 5 mm to 50 mm.

16. The reactor of claim 11, wherein:
    the catalyst bed comprises at least one monolithic body of one of a ceramic and metal material having pores or channels with a pore or channel size from 0.1 to 5 mm, and wherein the pores or channels contain an OCM catalyst powder.

17. The reactor of claim 16, wherein:
    the at least one monolithic body has a thickness of from 5 mm to 100 mm.

18. The reactor of claim 16, wherein:
    the catalyst powder has a particle size of less than 400 microns.

19. The reactor of claim 11, wherein:
    the OCM catalyst is selected from at least one of $La_2CeO_2$, $SrO/La_2O_3$, $CeO_2$, $La_2O_3$—$CeO_2$, $Ca/CeO_2$, $Mn/Na_2WO_4$, $Li_2O$, $Na_2O$, $Cs_2O$, $WO_3$, $Mn_3O_4$, CaO, MgO, SrO, BaO, CaO—MgO, CaO—BaO, Li/MgO, MnO, $W_2O_3$, $SnO_2$, $Yb_2O_3$, $Sm_2O_3$, $SrO/La_2O_3$, $La_2O_3$, $Ce_2O_3$, La/MgO, and combinations thereof.

\* \* \* \* \*